US009155317B2

(12) United States Patent
Stark et al.

(10) Patent No.: US 9,155,317 B2
(45) Date of Patent: Oct. 13, 2015

(54) ANTIFUNGAL COMPOSITIONS

(75) Inventors: Jacobus Stark, Echt (NL); Angelique De Rijk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 75 days.

(21) Appl. No.: 13/984,272

(22) PCT Filed: Feb. 8, 2012

(86) PCT No.: PCT/EP2012/052091
§ 371 (c)(1),
(2), (4) Date: Aug. 7, 2013

(87) PCT Pub. No.: WO2012/107466
PCT Pub. Date: Aug. 16, 2012

(65) Prior Publication Data
US 2013/0323387 A1    Dec. 5, 2013

(30) Foreign Application Priority Data

Feb. 9, 2011   (EP) .................................. 11153831

(51) Int. Cl.
*A01N 43/54*   (2006.01)
*A01N 43/90*   (2006.01)
*A23B 7/155*   (2006.01)
*A01N 3/00*    (2006.01)

(52) U.S. Cl.
CPC . *A23B 7/155* (2013.01); *A01N 3/00* (2013.01); *A01N 43/54* (2013.01); *A01N 43/90* (2013.01)

(58) Field of Classification Search
CPC ....... A23B 7/155; A01N 43/54; A01N 43/90; A01N 3/00
USPC ....................................................... 504/101
See application file for complete search history.

(56) References Cited

U.S. PATENT DOCUMENTS

| 5,597,598 A | 1/1997 | van Rijn et al. |
| 2009/0069356 A1* | 3/2009 | Bylemans et al. ............ 514/275 |
| 2011/0047654 A1 | 2/2011 | Stark et al. |

FOREIGN PATENT DOCUMENTS

| CN | 101978826 A | 2/2011 |
| CN | 101953352 B | 3/2013 |
| FR | 2828065 A1 | 2/2003 |
| WO | 9102518 A1 | 3/1991 |
| WO | 03011030 A1 | 2/2003 |
| WO | WO 2004036996 A1 * | 5/2004 |
| WO | 2005074684 A2 | 8/2005 |
| WO | 2009077613 A1 | 6/2009 |

OTHER PUBLICATIONS

Database WPI Week 201137, Thomson Scientific, London, GB: AN 2011-E14628, XP002653385, pp. 1-2, (2011).
International Search Report for PCT/EP2012/052091 Mailed May 9, 2012.
L. Kanetis et al., "Characterization of Genetic and Biochemical Mechanisms of Fludioxonil and Pyrimethanil Resistance in Field Isolates of *Penicillium digitatum*," Biochemistry and Cell Biology, The American Phytopathological Society, vol. 98, No. 2, pp. 205-214 (2008).
C. Moyano et al., "Resistance to Pyrimethanil and other Fungicides in *Botrytis cinerea* Populations Collected on Vegetable Crops in Spain," Department of Plant Protection, INIA, Madrid, Spain, Journal of Phytopathology, vol. 152, pp. 484-490 (2004).
C. L. Xiao et al., "Plant Disease: First Report of Occurrence of Pyrimethanil Resistance in *Penicillium expansum* from Stored Apples in Washington State," Tree Fruit Research and Extension Center, Washington Satte University, Wenatchee 98801, The American Phytopathological Society, vol. 95, No. 1, p. 72 (Jan. 2011), Retrieved online Sep. 3, 2013 from : http://apsjournals.apsnet.org/doi/abs/10.1094/PDIS-07-10-0509.

* cited by examiner

*Primary Examiner* — John Pak
*Assistant Examiner* — Andriae M Holt
(74) *Attorney, Agent, or Firm* — Miles & Stockbridge PC

(57) ABSTRACT

The present invention relates to new antifungal compositions and their use in the treatment of agricultural products.

17 Claims, No Drawings

ANTIFUNGAL COMPOSITIONS

CROSS REFERENCE TO RELATED APPLICATIONS

This application is a §371 National Stage Application of PCT/EP2012/052091, filed Feb. 8, 2012, which claims priority to European Application No. 11153831.0, filed Feb. 9, 2011.

BACKGROUND OF THE INVENTION

1. Field of the Invention

The present invention discloses new antimicrobial compositions to control plant diseases and to prevent microbial spoilage of crops.

2. Description of Related Art

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

Success in combating plant and crop diseases and in reducing the damage they cause to yields and quality depends greatly on the timely application of fungicides. The prolonged and frequent use of many fungicides such as e.g. benzamidazoles has contributed to reduce their effectiveness thanks to the development of phenomena of resistance.

Recently, new fungicides of other chemical families such as e.g. anilinopyrimidines have become commercially available (see WO 03/011030, FR 2 828 065 A1 and WO 2005/074684). Although these fungicides have shown activity against fungi, spoilage problems still occur. Moreover, several studies have shown that more and more fungi acquire resistance against these fungicides too (see Moyano et al. (2004), Kanetis et al. (2008), Xiao et al. (2011)). Furthermore, many of the currently used fungicides have the disadvantage of being dangerous for the health of exposed persons and the environment.

For many decades, fungicides have also been used to prevent fungal growth on food products such as cheeses and sausages. EP 0 986 965 A1 describes the use of imazalil sulphate to treat cheeses and sausages and protect them against fungal growth. U.S. Pat. No. 5,597,598 describes the combined treatment of food products with two acids and the polyene macrolide antimycotic natamycin. This natural preservative, which is produced by fermentation using *Streptomyces natalensis*, is widely used throughout the world as a food preservative and has a long history of safe use in the food industry. It is very effective against all known food spoilage fungi. Although natamycin has been applied for many years in e.g. the cheese industry, up to now development of resistant fungal species was never observed.

Consequently, it can be concluded that there is a severe need for more effective, more environmental friendly, lower-toxicity and less harmful antimicrobial compositions, e.g. antifungal compositions, for the treatment of fungal growth in and on plants and crops.

SUMMARY

The present invention solves the problem by providing a new synergistic antimicrobial, e.g. antifungal, composition comprising a polyene antifungal compound and at least one antifungal compound from the family of anilinopyrimidines. As used herein, the term "synergistic" means that the combined effect of the antifungal compounds when used in combination is greater than their additive effects when used individually.

In general, synergistic activity of two active ingredients can be tested in for example the analysis of variance model using the treatment interaction stratum (see Slinker, 1998). Relative efficacy can be calculated by means of the following formula: ((value of evolution status of untreated control−value of evolution status of composition)/(value of evolution status of untreated control))*100. An interaction coefficient can then be calculated by means of the following formula: ((relative efficacy of combination compound A+compound B)/(relative efficacy of compound A+relative efficacy of compound B))*100. An interaction coefficient larger than 100 indicates synergy between the compounds.

Alternatively, synergy can be calculated as follows: the antifungal activity (in %) of the individual active ingredients can be determined by calculating the reduction in mould growth observed on products treated with the active ingredients in comparison to the mould growth on products treated with a control composition. The expected antifungal activity (E in %) of the combined antifungal composition comprising both active ingredients can be calculated according to the Colby equation (Colby, 1967): $E = X + Y − [(X \cdot Y)/100]$, wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

DETAILED DESCRIPTION OF A PREFERRED EMBODIMENT

In an embodiment of the invention, the at least one antifungal compound from the family of anilinopyrimidines is selected from the group consisting of cyprodinil, mepanipyrim and pyrimethanil. In an embodiment the compositions may also contain two or more different antifungal compounds from the family of anilinopyrimidines. It is to be understood that derivatives of antifungal compounds from the family of anilinopyrimidines including, but not limited to, salts or solvates of antifungal compounds from the family of anilinopyrimidines or modified forms of antifungal compounds from the family of anilinopyrimidines may also be applied in the compositions of the invention. Examples of commercial products containing anilinopyrimidines such as pyrimethanil are the products with the brand name Mythos® (pyrimethanil), Scala® (pyrimethanil), Siganex® (pyrimethanil) or Walabi® (pyrimethanil and chlorthalonil). Said commercial products can be incorporated in the present invention.

In an embodiment the polyene antifungal compound is selected from the group consisting of natamycin, nystatin, amphotericin B, trienin, etruscomycin, filipin, chainin, dermostatin, lymphosarcin, candicidin, aureofungin A, aureofungin B, hamycin A, hamycin B and lucensomycin. In a preferred embodiment the polyene antifungal compound is natamycin. In an embodiment the compositions may also contain two or more different polyene antifungal compounds. It is to be understood that derivatives of polyene antifungal compounds including, but not limited to, salts or solvates of polyene antifungal compounds or modified forms of polyene antifungal compounds may also be applied in the compositions of the invention. Examples of commercial products containing natamycin are the products with the brand name Delvocid®. Such products are produced by DSM Food Specialties (The Netherlands) and may be solids containing e.g. 50% (w/w) natamycin or liquids comprising between e.g. 2-50% (w/v) natamycin. Said commercial products can be incorporated in the compositions of the invention.

The composition of the present invention generally comprises from about 0.005 g/l to about 100 g/l and preferably from about 0.01 g/l to about 50 g/l of a polyene antifungal compound. Preferably, the amount is from 0.01 g/l to 3 g/l.

The composition of the present invention generally comprises from about 0.0001 g/l to about 2000 g/l and preferably from about 0.0005 g/l to about 1500 g/l of an antifungal compound from the family of anilinopyrimidines. More preferably, the amount is from 0.001 g/l to 1000 g/l.

In an embodiment the composition of the present invention further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant. A further antimicrobial antifungal compound may be an antifungal compound (e.g. imazalil, thiabendazole or chlorthalonil) or a compound to combat insects, nematodes, mites and/or bacteria. Of course, the compositions according to the invention may also comprise two or more of any of the above additional compounds. Any of the above mentioned additional compounds may also be combined with the polyene antifungal compound and/or the at least one antifungal compound from the family of anilinopyrimidines in case the antifungal compounds are applied separately. In an embodiment the additional compounds are additives acceptable for the specific use, e.g. food, feed, medicine, cosmetics or agriculture. Additional compounds suitable for use in food, feed, medicine, cosmetics or agriculture are known to the person skilled in the art.

In a specific embodiment the further antimicrobial compound is a natural crop protection compound belonging to the group of phosphites, e.g. $KH_2PO_3$ or $K_2HPO_3$ or a mixture of both phosphite salts. Phosphite containing compounds as used herein means compounds comprising a phosphite group, i.e. $PO_3$ (in the form of e.g. $H_2PO_3^-$, $HPO_3^{2-}$ or $PO_3^{3-}$) or any compound which allows the release of a phosphite ion including compounds such as phosphorous acid and phosphonic acid as well as derivatives thereof such as esters and/or alkali metal or alkaline earth metal salts thereof. In case the compositions of the present invention comprise a polyene antifungal compound (e.g. natamycin) and at least one phosphite containing compound, they preferably comprise 0.1 g or less lignosulphonate, more preferably 0.1 g or less polyphenol, per gram polyene antifungal compound. Preferably, they comprise 0.01 g or less lignosulphonate, more preferably 0.01 g or less polyphenol, per gram polyene antifungal compound. In particular, they are free of lignosulphonate and preferably free of polyphenol. Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and ($C_1$-$C_4$) alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in the crop or plant are metabolized into phosphite compounds can also be included in the compositions of the present invention. Examples are phosphonates such as the fosetyl-aluminium complex. In e.g. a crop or plant the ethyl phosphonate part of this molecule is metabolized into a phosphite. An example of such a compound in the commercial ethyl hydrogen phosphonate product called Aliette® (Bayer, Germany). The ratio of phosphite to natamycin (in weight) in the compositions is in general between 2:1 to 500:1 (w/w), preferably between 3:1 to 300:1 (w/w) and more preferably between 5:1 to 200:1 (w/w).

Compositions according to the invention may have a pH of from 1 to 10, preferably of from 2 to 9, more preferably of from 3 to 8 and most preferably of from 4 to 7. They may be solid, e.g. powder compositions, or may be liquid. The compositions of the present invention can be aqueous or non-aqueous ready-to-use compositions, but may also be aqueous or non-aqueous concentrated compositions/suspensions or stock compositions, suspensions and/or solutions which before use have to be diluted with a suitable diluent such as water or a buffer system. Alternatively, the compositions of the invention can also be used to prepare coating emulsions. The compositions of the present invention can also have the form of concentrated dry products such as e.g. powders, granulates and tablets. They can be used to prepare compositions for immersion or spraying of products such as agricultural products including plants, crops, vegetables and/or fruits. Of course, the above is also applicable when the polyene antifungal compound and the at least one antifungal compound from the family of anilinopyrimidines are applied as separate compositions.

In a further aspect the invention relates to a kit comprising a polyene antifungal compound and at least one antifungal compound from the family of anilinopyrimidines. The polyene antifungal compound and the at least one antifungal compound from the family of anilinopyrimidines may be present in two separate packages, e.g. containers. The components of the kit may be either in dry form or liquid form in the package. If necessary, the kit may comprise instructions for dissolving the compounds. In addition, the kit may contain instructions for applying the compounds.

In a further aspect the invention pertains to a method for protecting a product against fungi by treating the agricultural product with a polyene antifungal compound and at least one antifungal compound from the family of anilinopyrimidines. In addition, the product can be treated with other antifungal and/or antimicrobial compounds either prior to, concomitant with or after treatment of the products with the polyene antifungal compound and the at least one antifungal compound from the family of anilinopyrimidines. The product may be treated by sequential application of the polyene antifungal compound and the at least one antifungal compound from the family of anilinopyrimidines or vice versa. Alternatively, the product may be treated by simultaneous application of the polyene antifungal compound and the at least one antifungal compound from the family of anilinopyrimidines. In case of simultaneous application, the compounds can be present in different compositions that are applied simultaneously or the compounds may be present in a single composition. In yet another embodiment the product may be treated by separate or alternate modes of applying the antifungal compounds. In an embodiment the invention is directed to a process for the treatment of products by applying the polyene antifungal compound and the at least one antifungal compound from the family of anilinopyrimidines to the products. By applying the compounds fungal growth on or in the products can be prevented. In other words, the compounds protect the products from fungal growth and/or from fungal infection and/or from fungal spoilage. The compounds can also be used to treat products that have been infected with a fungus. By applying the compounds the disease development due to fungi on or in these products can be slowed down, stopped or the products may even be cured from the disease. In an embodiment of the invention the products are treated with a composition or kit according to the invention. In an embodiment the product is a food, feed, pharmaceutical, cosmetic or agricultural product. In a preferred embodiment the product is an agricultural product.

The polyene antifungal compound and the at least one antifungal compound from the family of anilinopyrimidines, the compositions according to the invention and the kits according to the invention can be applied to the products by spraying. Other methods suitable for applying these compounds, compositions and kits in liquid form to the products are also a part of the present invention. These include, but are not limited to, dipping, watering, drenching, introduction into a dump tank, vaporizing, atomizing, fogging, fumigating, painting, brushing, dusting, foaming, spreading-on, packaging and coating (e.g. by means of wax or electrostatically). In addition, the antifungal compounds may also be injected into the soil. Spraying applications using automatic systems are known to reduce the labour costs and are cost-effective. Methods and equipment well-known to a person skilled in the art can be used for that purpose. The compositions according to the invention can be regularly sprayed, when the risk of infection is high. When the risk of infection is lower spray intervals may be longer. Depending on the type of application, the amount of polyene antifungal compound applied may vary from 5 ppm to 10,000 ppm, preferably from 10 ppm to 5,000 ppm and most preferably from 20 to 1,000 ppm. Depending on the type of application, the amount of the at least one antifungal compound from the family of anilinopyrimidines applied may vary from 10 ppm to 5,000 ppm, preferably from 20 ppm to 3,000 ppm and most preferably from 50 to 1,000 ppm.

In a specific embodiment the agricultural product can be treated post-harvest. By using a polyene antifungal compound and the at least one antifungal compound from the family of anilinopyrimidines the control of post-harvest and/or storage diseases is achieved for a long period of time to allow transport of the harvested agricultural product over long distances and under various storage conditions with different controlled atmosphere systems in respect of temperature and humidity. Post-harvest storage disorders are e.g. lenticel spots, scorch, senescent breakdown, bitter pit, scald, water core, browning, vascular breakdown, $CO_2$ injury, $CO_2$ or $O_2$ deficiency, and softening. Fungal diseases may be caused for example by the following fungi: *Mycosphaerella* spp., *Mycosphaerella musae, Mycosphaerella fragariae, Mycosphaerella citri; Mucor* spp., e.g. *Mucor piriformis; Monilinia* spp., e.g. *Monilinia fructigena, Monilinia laxa; Phomopsis* spp., *Phomopsis natalensis; Colletotrichum* spp., e.g. *Colletotrichum musae, Colletotrichum gloeosporioides, Colletotrichum coccodes; Verticillium* spp., e.g. *Verticillium theobromae; Nigrospora* spp.; *Botrytis* spp., e.g. *Botrytis cinerea; Dipodia* spp., e.g. *Dipodia citri; Pezicula* spp.; *Alternaria* spp., e.g. *Alternaria citri, Alternaria alternata; Septoria* spp., e.g. *Septoria depressa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Fusarium* spp., e.g. *Fusarium semitectum, Fusarium moniliforme, Fusarium solani, Fusarium oxysporum; Cladosporium* spp., e.g. *Cladosporium fulvum, Cladosporium cladosporioides, Cladosporium cucumerinum, Cladosporium musae; Penicillium* spp., e.g. *Penicillium funiculosum, Penicillium expansum, Penicillium digitatum, Penicillium italicum; Phytophthora* spp., e.g. *Phytophthora citrophthora, Phytophthora fragariae, Phytophthora cactorum, Phytophthora parasitica; Phacydiopycnis* spp., e.g. *Phacydiopycnis malirum; Gloeosporium* spp., e.g. *Gloeosporium album, Gloeosporium perennans, Gloeosporium fructigenum, Gloeosporium singulata; Geotrichum* spp., e.g. *Geotrichum candidum; Phlyctaena* spp., e.g. *Phlyctaena vagabunda; Cylindrocarpon* spp., e.g. *Cylindrocarpon mali; Stemphyllium* spp., e.g. *Stemphyllium vesicarium; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeae-maydis*.

Another aspect of the present invention relates to the use of a polyene antifungal compound and at least one antifungal compound from the family of anilinopyrimidines to protect a product against fungi. As indicated above, the compounds may be used, e.g. applied, sequentially or simultaneously. In an embodiment the invention relates to a use, wherein a composition or kit according to the invention is applied to the product. In an embodiment the product is a food, feed, pharmaceutical, cosmetic or agricultural product. In a preferred embodiment the product is an agricultural product.

A further aspect of the invention is directed to a product treated with a polyene antifungal compound and at least one antifungal compound from the family of anilinopyrimidines. In an embodiment the product is treated with a composition or kit according to the invention. The invention is therefore directed to a product comprising a polyene antifungal compound and at least one antifungal compound from the family of anilinopyrimidines. The treated products may comprise a polyene antifungal compound and at least one antifungal compound from the family of anilinopyrimidines on their surface and/or inside the product. Alternatively, the treated products may comprise a coating comprising these compounds. In an embodiment the treated products comprise from 0.000001 to 200 mg/dm$^2$, preferably 0.00001 to 100 mg/dm$^2$, more preferably from 0.00005 to 10 mg/dm$^2$ of the polyene antifungal compound on their surface. In a further embodiment they comprise from 0.000001 to 200 mg/dm$^2$, preferably 0.00001 to 100 mg/dm$^2$, more preferably from 0.00005 to 10 mg/dm$^2$ of the at least one antifungal compound from the family of anilinopyrimidines on their surface. In an embodiment the product is a food, feed, pharmaceutical, cosmetic or agricultural product. In a preferred embodiment the product is an agricultural product.

The term "food products" as used herein is to be understood in a very broad sense and includes, but is not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products.

The term "feed products" as used herein is also to be understood in a very broad sense and includes, but is not limited to, pet food, broiler feed, etc.

The term "pharmaceutical product" as used herein is also to be understood in a very broad sense and includes products comprising an active molecule such as a drug, agent, or pharmaceutical compound and optionally a pharmaceutically acceptable excipient, i.e. any inert substance that is combined with the active molecule for preparing an agreeable or convenient dosage form.

The term "cosmetic product" as used herein is also to be understood in a very broad sense and includes products that are used for protecting or treating horny tissues such as skin and lips, hair and nails from drying by preventing transpiration of moisture thereof and further conditioning the tissues as well as giving good appearance to these tissues. Products contemplated by the term "cosmetic product" include, but are not limited to, moisturizers, personal cleansing products, occlusive drug delivery patches, nail polish, powders, wipes, hair conditioners, skin treatment emulsions, shaving creams and the like.

The term "agricultural products" as used herein is also to be understood in a very broad sense and includes, but is not limited to, cereals, e.g. wheat, barley, rye, oats, rice, sorghum and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts, coffee, sugarcane, tea, grapevines, hops, rubber plants, as well as ornamental plants, e.g. cut flowers, roses, tulips, lilies, narcissus, crocuses, hyacinths, dahlias, gerbera, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

A method for preparing a composition as described herein is another aspect of the present invention. The method comprises adding a polyene antifungal compound to at least one antifungal compound from the family of anilinopyrimidines. The compounds may for instance be added separately to an aqueous composition and mixed, followed, if necessary, by adjustment of the pH, viscosity, etc. If added separately, some or all of the separate compounds may be in powder form, but alternatively some or all may also be in liquid form. The compounds may for instance also be added to one another in powder form and mixed to obtain a powdered composition. The powdered composition may then be added to an aqueous composition.

Example 1

Pre-Harvest Application

Leaves of banana plants are inoculated with fungi. As a control non-inoculated leaves are also included. Next, a defined part of the leaves are treated with composition 1 (natamycin), composition 2 (pyrimethanil) or composition 3 (natamycin+pyrimethanil). Each composition is applied by spraying. Untreated leaves are also included (untreated control).

The obtained results show that the compositions of the present invention protect banana plants from fungal growth and further demonstrate that the compositions of the present invention show a synergistically enhanced activity compared to the activity of the active compounds when applied individually.

Example 2

Post-Harvest Application

Bananas are injured according to the method described by de Lapeyre de Bellaire and Dubois (1987). Bananas are wounded using a cork borer followed by contamination with fungal spores. After incubation for several hours at room temperature, the bananas are dipped in one of the following compositions: a) no treatment (control 1), b) dipped in water (control 2), c) dipped in natamycin, d) dipped in pyrimethanil, e) dipped in natamycin+pyrimethanil. After this treatment the bananas are incubated in closed boxes at 21° C. at elevated humidity. Each day the bananas are judged visually on fungal development.

The results show that the composition comprising natamycin and pyrimethanil protects bananas better against fungi than natamycin or pyrimethanil alone. Surprisingly, the combined application of natamycin and pyrimethanil leads to a strong synergistic reduction in infection.

Example 3

Treatment of Bananas

Four organic, unripe (green) bananas were used per treatment. The peel of each banana was wounded thrice using a cork borer according to the method described by de Lapeyre de Bellaire and Dubois (1987). Subsequently, each wound was inoculated with 15 µl of a *Fusarium proliferatum* suspension containing $1 \times 10^5$ of spores/ml. After incubation for 4 hours at 20° C., each banana wound was treated with 100 µl of a freshly prepared aqueous antifungal composition comprising either 500 ppm natamycin (DSM Food Specialties, Delft, The Netherlands), 1000 ppm cyprodinil or both. In addition, the antifungal compositions comprised 1.00% (w/w) methylhydroxyethylcellulose (MHEC), 0.40% (w/w) xanthan gum, 0.20% (w/w) anti-foaming agent, 0.30% (w/w) citric acid, 0.39% (w/w) lactic acid and 0.11% (w/w) potassium sorbate. A composition without natamycin or cyprodinil was used as control. The treated, unripe bananas were incubated in a closed box in the dark at 20° C. and a relative air humidity of 95%, which was obtained in the presence of a saturated $Na_2HPO_4$ aqueous solution. During the first 20 days of incubation, a ripe (yellow) banana was included in the closed box to elevate the ethylene gas level and thus induce ripening of the treated, unripe bananas.

During incubation, the degree of mould growth on the bananas was assessed in a twofold manner: (i) the number of moulded wounds per total of 12 wounds was counted; and (ii) the antifungal activity (in %) of the individual active ingredients was determined by calculating the reduction in mould growth observed on the banana wounds treated with the antifungal composition in comparison to the mould growth on the banana wounds treated with the control composition. The expected antifungal activity (E in %) of the combined antifungal composition comprising both active ingredients was calculated according to the Colby equation (Colby, 1967):

$$E=X+Y-[(X \cdot Y)/100]$$

wherein X and Y are the observed antifungal activities (in %) of the individual active ingredients X and Y, respectively. If the observed antifungal activity (0 in %) of the combination exceeds the expected antifungal activity (E in %) of the combination and the synergy factor O/E is thus >1.0, the combined application of the active ingredients leads to a synergistic antifungal effect.

The results in Table 1 (number of moulded wounds per total of 12 wounds) and Table 2 (antifungal activity) clearly demonstrate that the antifungal composition comprising both 500 ppm natamycin and 1000 ppm cyprodinil protected bananas better against mould growth than natamycin or cyprodinil alone.

After 23 days of incubation, all 12 wounds treated with the control composition or with cyprodinil alone showed mould growth, whereas 9 of the 12 wounds treated with natamycin alone were moulded. However, mould growth was observed only for 6 of the 12 wounds treated with the composition comprising both natamycin and cyprodinil (see Table 1).

After 27 days of incubation, all 12 wounds treated with either the control composition, natamycin alone or cyprodinil alone showed mould growth. However, mould growth was observed only for 7 of the 12 wounds treated with the composition comprising both natamycin and cyprodinil (see Table 1). Furthermore, the observed antifungal activity of the composition comprising both natamycin and cyprodinil was 13% higher than the expected antifungal activity and a synergy factor of >1.0 was obtained (see Table 2).

After 39 days of incubation, the observed antifungal activity of the composition comprising both natamycin and cyprodinil was 6% higher than the expected antifungal activity and a synergy factor of >1.0 was obtained (see Table 2).

Hence, the combination of 500 ppm natamycin and 1000 ppm cyprodinil has synergistic antifungal activity on bananas.

Example 4

Treatment of Bananas

The experiment was conducted as described in Example 3, except for the fact that each inoculated banana wound was treated with 100 µl of a freshly prepared aqueous antifungal composition comprising either 250 ppm natamycin (DSM Food Specialties, Delft, The Netherlands), 500 ppm cyprodinil or both. The degree of mould growth on the banana wounds was assessed according to the two methods described in Example 3.

The results in Table 3 (number of moulded wounds per total of 12 wounds) and Table 4 (antifungal activity) reveal that the antifungal composition comprising 250 ppm natamycin as well as 500 ppm cyprodinil was superior to the compositions comprising either natamycin alone or cyprodinil alone in reducing mould growth on bananas.

After 18 and 21 days of incubation, all 12 wounds treated with either the control composition, natamycin alone or cyprodinil alone showed mould growth. However, when treated with the composition comprising both natamycin and cyprodinil, only 6 of the 12 wounds were moulded after 18 days and 7 of the 12 wounds were moulded after 21 days (see Table 3).

Furthermore, after 21 days of incubation the actually observed antifungal activity of the composition comprising both natamycin and cyprodinil was 23% higher than the expected antifungal activity, which resulted in a synergy factor of 1.5 (see Table 4).

Moreover, after 32 and 34 days of incubation, the observed antifungal activity of the composition comprising both natamycin and cyprodinil was 30% higher than the expected antifungal activity. Consequently, the synergy factors far exceeded 1.0 (see Table 4).

In conclusion, the results of this example clearly demonstrate that the antifungal activity of the combination of 250 ppm natamycin and 500 ppm cyprodinil when applied on bananas is highly synergistic.

Example 5

Treatment of Bananas

The experiment was conducted as described in Example 3, except for the fact that each inoculated banana wound was treated with 100 µl of a freshly prepared aqueous antifungal composition comprising either 50 ppm natamycin (DSM Food Specialties, Delft, The Netherlands), 250 ppm cyprodinil or both. The antifungal activity (in %) of the individual and combined active ingredients on the banana wounds was determined according to the method described in Example 3.

The results (see Table 5) show that the combined antifungal composition comprising 50 ppm natamycin and 250 ppm cyprodinil protected bananas more effectively against mould growth than the compositions comprising natamycin or cyprodinil alone.

After 23, 29, 32 and 36 days of incubation, the observed antifungal activity of the composition comprising both natamycin and cyprodinil was 10 to 21% higher than the expected antifungal activity. The synergy factor ranged from 2.3 to >10 after 23 and 36 days of incubation, respectively.

Thus, the combined application of 50 ppm natamycin and 250 ppm cyprodinil leads to a surprisingly strong synergistic reduction in mould growth on bananas.

Example 6

Treatment of bananas

The experiment was conducted as described in Example 3, except for the fact that each inoculated banana wound was treated with 100 µl of a freshly prepared aqueous antifungal composition comprising either 250 ppm natamycin (DSM Food Specialties, Delft, The Netherlands), 500 ppm pyrimethanil or both. A composition without natamycin or pyrimethanil was used as control. The antifungal activity (in %) of the individual and combined active ingredients on the banana wounds was determined according to the method described in Example 3.

The results (see Table 6) clearly demonstrate that the combined antifungal composition comprising 250 ppm natamycin and 500 ppm pyrimethanil had a much stronger antifungal activity on bananas than the compositions comprising natamycin or pyrimethanil alone.

After 23, 29, 32 and 34 days of incubation, the observed antifungal activity of the composition comprising both natamycin and pyrimethanil was 4 to 11% higher than the expected antifungal activity. As a result, all synergy factors exceeded 1.0 and increased from 1.5 on day 23 to >11 on day 34.

Hence, the antifungal activity of the combination of 250 ppm natamycin and 500 ppm pyrimethanil is strongly synergistic when applied on bananas.

Example 7

Treatment of Strawberries

Twelve fresh, organic strawberries were used per treatment. Each strawberry was wounded with a 0.5 mm long cut and each wound was inoculated with 10 µl of a *Botrytis cinerea* suspension containing $1 \times 10^5$ of spores/ml. After a 2-hour incubation period at 20° C., each strawberry was dipped individually for 1 minute in a freshly prepared aqueous antifungal composition comprising either 250 ppm natamycin (DSM Food Specialties, Delft, The Netherlands), 500 ppm pyrimethanil or both. The antifungal composition also comprised 1.00% (w/w) methylhydroxyethylcellulose (MHEC), 0.40% (w/w) xanthan gum, 0.20% (w/w) anti-foaming agent, 0.30% (w/w) citric acid, 0.39% (w/w) lactic acid and 0.11% (w/w) potassium sorbate. A composition without natamycin or pyrimethanil was used as control.

The treated strawberries were incubated for three days in a closed box in the dark at 20° C. and assessed daily on mould growth. The antifungal activity (in %) of the individual active ingredients was determined by calculating the reduction in mould growth observed on the strawberries treated with the antifungal composition in comparison to the mould growth on the strawberries treated with the control composition. The expected antifungal activity (E in %) of the combined antifungal composition comprising both active ingredients was calculated according to the Colby equation (Colby, 1967):

$$E=X+Y-[(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results (see Table 7) show that the antifungal composition comprising 250 ppm natamycin and 500 ppm pyrimethanil protected strawberries much better against mould growth than natamycin or pyrimethanil alone.

After 1, 2 and 3 days of incubation, the observed antifungal activity of the combined composition comprising natamycin and pyrimethanil was respectively 25, 21 and 14% higher than the expected antifungal activity. The corresponding synergy factors ranged from 1.6 to 2.0.

Hence, the combined application of 250 ppm natamycin and 500 ppm pyrimethanil leads to a synergistic reduction in mould growth on strawberries.

Example 8

Treatment of Mandarins

Ten fresh, organic mandarins were used per treatment. The peel of each mandarin was wounded once using a cork borer according to the method described by de Lapeyre de Bellaire and Dubois (1987). Subsequently, each wound was inoculated with 10 µl of a *Penicillium italicum* suspension containing $1 \times 10^4$ of spores/ml. After incubation for 2 hours at 20° C., the mandarins were dipped individually for 1 minute in a freshly prepared aqueous antifungal composition comprising either 250 ppm natamycin (DSM Food Specialties, Delft, The Netherlands), 500 ppm cyprodinil or both. In addition, the antifungal composition comprised 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) anti-foaming agent, 0.15% (w/w) citric acid and 0.01% (w/w) potassium sorbate. A composition without natamycin or cyprodinil was used as control.

The treated mandarins were incubated in a closed box in the dark at 20° C. and assessed on mould growth after 16, 19, 22 and 26 days of incubation. The antifungal activity (in %) of the individual active ingredients was determined by calculating the reduction in mould growth observed on the mandarins treated with the antifungal composition in comparison to the mould growth on the mandarins treated with the control composition. The expected antifungal activity (E in %) of the combined antifungal composition comprising both active ingredients was calculated according to the Colby equation (Colby, 1967):

$$E=X+Y-[(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results (see Table 8) clearly demonstrate that the antifungal composition comprising 250 ppm natamycin and 500 ppm cyprodinil was superior to the compositions comprising natamycin or cyprodinil alone in preventing mould growth on mandarins.

After 16, 19, 22 and 26 days of incubation, the observed antifungal activity of the composition comprising both natamycin and cyprodinil was 31 to 62% higher than the expected antifungal activity. Consequently, all synergy factors exceeded 1.0 and increased from 1.5 on day 16 to 4.3 on day 26.

Hence, the results of this example clearly demonstrate the synergistic antifungal activity between 250 ppm natamycin and 500 ppm cyprodinil on mandarins.

Example 9

Treatment of Mandarins

The experiment was conducted as described in Example 8, except for the fact that each wounded, inoculated mandarin was dipped individually for 1 minute in a freshly prepared aqueous antifungal composition comprising either 500 ppm natamycin (DSM Food Specialties, Delft, The Netherlands), 1000 ppm pyrimethanil or both. A composition without natamycin or pyrimethanil was used as control. The antifungal activity (in %) of the individual and combined active ingredients on the banana wounds was assessed after 22 and 26 days of incubation according to the method described in Example 8.

The results in Table 9 prove that the antifungal composition comprising 500 ppm natamycin and 1000 ppm pyrimethanil reduced mould growth on mandarins more effectively than natamycin or pyrimethanil alone.

After 22 and 26 days of incubation, the observed antifungal activity of the composition comprising both natamycin and pyrimethanil exceeded the expected antifungal activity with respectively 11 and 13% and synergy factors >1.0 were obtained.

It can therefore be concluded that the combined application of 500 ppm natamycin and 1000 ppm pyrimethanil leads to a synergistic reduction in mould growth on mandarins.

Example 10

Treatment of Mandarins

The experiment was conducted as described in Example 8, except for the fact that each wounded, inoculated mandarin was dipped individually for 1 minute in a freshly prepared aqueous antifungal composition comprising either 250 ppm natamycin (DSM Food Specialties, Delft, The Netherlands), 500 ppm pyrimethanil or both. A composition without natamycin or pyrimethanil was used as control. The antifungal activity (in %) of the individual and combined active ingredients on the banana wounds was assessed after 19, 22 and 26 days of incubation according to the method described in Example 8. The results (see Table 10) reveal that the antifungal composition comprising 500 ppm natamycin and 1000 ppm pyrimethanil had a stronger antifungal activity on mandarins than the compositions comprising natamycin or pyrimethanil alone.

After 19, 22 and 26 days of incubation, the observed antifungal activity of the composition comprising both natamycin and pyrimethanil exceeded the expected antifungal activity with 15, 21 and 29%, respectively, and synergy factors >1.0 were obtained.

In conclusion, the antifungal activity of the active ingredient combination of 250 ppm natamycin and 500 ppm pyrimethanil is synergistic when applied on mandarins.

Example 11

In Vitro Antifungal Activity

To show synergistic activity of the combination of natamycin with cyprodinil or pyrimethanil, an in vitro assay was conducted using 96-well microtiter plates. The following compositions were tested:
Control (no active ingredient),
0.63 ppm of natamycin (DSM Food Specialties, Delft, The Netherlands),
1.25 ppm of natamycin,
10 ppm of cyprodinil,
20 ppm of cyprodinil,
17.5 ppm of pyrimethanil,
30 ppm of pyrimethanil,
0.63 ppm of natamycin+20 ppm of cyprodinil,
0.63 ppm of natamycin+30 ppm of pyrimethanil,
1.25 ppm of natamycin+10 ppm of cyprodinil
1.25 ppm of natamycin+17.5 ppm of pyrimethanil.

After filling each well with 92 μl of PCB medium, natamycin and cyprodinil or pyrimethanil were added from separate stock solutions prepared in PCB medium or methanol, which resulted in an intermediate volume of 100 μl per well. Subsequently, 100 μl of a *Botrytis cinerea* suspension prepared in PCB medium was used to inoculated each well with $2.5 \times 10^3$ spores/ml. Each well thus contained a final volume of 200 μl and <1% of methanol, which did not affect fungal growth (data not shown).

After incubation of the microtiter plates for 5 days at 25° C., the in vitro antifungal activity (%) of the individual active ingredients was assessed by calculating the reduction in mould growth observed in the presence of the active ingredient in comparison to the mould growth observed in the absence of the active ingredient. The expected antifungal activity (E in %) of the active ingredient combination was calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the resulting synergy factor O/E is thus >1.0, the combined application of the active ingredients leads to a synergistic antifungal effect.

The results (see Table 11) demonstrate that the combinations natamycin+cyprodinil and natamycin+pyrimethanil had much stronger antifungal activities against *Botrytis cinerea* than natamycin, cyprodinil and pyrimethanil individually. Moreover, the observed antifungal activities of the combinations natamycin+cyprodinil and natamycin+pyrimethanil were 50 to 100% higher than the expected antifungal activities, resulting in synergy factors far above 1.0.

Hence, the combined application of natamycin and cyprodinil as well as the combined application of natamycin and pyrimethanil synergistically inhibit growth of *Botrytis cinerea*.

Example 12

In Vitro Antifungal Activity

The experiment was conducted as described in Example 11, except for the fact that the following compositions were tested:
Control (no active ingredient),
1.25 ppm of natamycin (DSM Food Specialties, Delft, The Netherlands),
125 ppm of cyprodinil,
1.25 ppm of natamycin+125 ppm of cyprodinil,
2.5 ppm of natamycin,
275 ppm of pyrimethanil,
2.5 ppm of natamycin+275 ppm of pyrimethanil.

Furthermore, *Fusarium proliferatum* was used for inoculation. The antifungal activity (in %) of the individual and combined active ingredients was determined according to the method described in Example 11.

The results (see Table 12) reveal that the active ingredient combinations natamycin+cyprodinil and natamycin+pyrimethanil inhibit growth of *Fusarium proliferatum* more effectively than natamycin, cyprodinil and pyrimethanil individually. Moreover, the observed antifungal activities of the active ingredient combinations natamycin+cyprodinil and natamycin+pyrimethanil were 100% higher than the expected antifungal activities, resulting in synergy factors far above 1.0.

Hence, the combined application of natamycin and cyprodinil and the combined application of natamycin and pyrimethanil both lead to a strong synergistic reduction in the growth of *Fusarium proliferatum*.

TABLE 1

Number of moulded wounds on bananas incubated at 20° C. after treatment with compositions comprising either 500 ppm natamycin, 1000 ppm cyprodinil or both.

| Antifungal composition | Incubation time (days) | Number of moulded wounds/ total number of 12 wounds |
| --- | --- | --- |
| Control | 23 | 12/12 |
| Natamycin 500 ppm | | 9/12 |
| Cyprodinil 1000 ppm | | 12/12 |
| Natamycin 500 ppm + cyprodinil 1000 ppm | | 6/12 |
| Control | 27 | 12/12 |
| Natamycin 500 ppm | | 12/12 |

TABLE 1-continued

Number of moulded wounds on bananas incubated at 20° C. after treatment with compositions comprising either 500 ppm natamycin, 1000 ppm cyprodinil or both.

| Antifungal composition | Incubation time (days) | Number of moulded wounds/ total number of 12 wounds |
|---|---|---|
| Cyprodinil 1000 ppm | | 12/12 |
| Natamycin 500 ppm + cyprodinil 1000 ppm | | 7/12 |

TABLE 2

Antifungal activity (%) of compositions comprising either 500 ppm natamycin, 1000 ppm cyprodinil or both on bananas incubated at 20° C.

| Antifungal composition | Incubation time (days) | Observed antifungal activity O (%) | Expected antifungal activity E (%) | Synergy factor O/E |
|---|---|---|---|---|
| Control | 27 | 0 | — | — |
| Natamycin 500 ppm | | 63 | — | — |
| Cyprodinil 1000 ppm | | 18 | — | — |
| Natamycin 500 ppm + cyprodinil 1000 ppm | | 83 | 70 | 1.2 |
| Control | 39 | 0 | — | — |
| Natamycin 500 ppm | | 11 | — | — |
| Cyprodinil 1000 ppm | | 0 | — | — |
| Natamycin 500 ppm + cyprodinil 1000 ppm | | 17 | 11 | 1.6 |

TABLE 3

Number of moulded wounds on bananas incubated at 20° C. after treatment with compositions comprising either 250 ppm natamycin, 500 ppm cyprodinil or both.

| Antifungal composition | Incubation time (days) | Number of moulded wounds/ total number of 12 wounds |
|---|---|---|
| Control | 18 | 12/12 |
| Natamycin 250 ppm | | 12/12 |
| Cyprodinil 500 ppm | | 12/12 |
| Natamycin 250 ppm + cyprodinil 500 ppm | | 6/12 |
| Control | 21 | 12/12 |
| Natamycin 250 ppm | | 12/12 |
| Cyprodinil 500 ppm | | 12/12 |
| Natamycin 250 ppm + cyprodinil 500 ppm | | 7/12 |

TABLE 4

Antifungal activity (%) of compositions comprising either 250 ppm natamycin, 500 ppm cyprodinil or both on bananas incubated at 20° C.

| Antifungal composition | Incubation time (days) | Observed antifungal activity O (%) | Expected antifungal activity E (%) | Synergy factor O/E |
|---|---|---|---|---|
| Control | 21 | 0 | — | — |
| Natamycin 250 ppm | | 10 | — | — |
| Cyprodinil 500 ppm | | 35 | — | — |
| Natamycin 250 ppm + cyprodinil 500 ppm | | 64 | 41 | 1.5 |
| Control | 32 | 0 | — | — |
| Natamycin 250 ppm | | 2 | — | — |
| Cyprodinil 500 ppm | | 3 | — | — |
| Natamycin 250 ppm + cyprodinil 500 ppm | | 36 | 5 | 7.0 |
| Control | 34 | 0 | — | — |
| Natamycin 250 ppm | | 0 | — | — |
| Cyprodinil 500 ppm | | 0 | — | — |
| Natamycin 250 ppm + cyprodinil 500 ppm | | 30 | 0 | >30 |

TABLE 5

Antifungal activity (%) of compositions comprising either 50 ppm natamycin, 250 ppm cyprodinil or both on bananas incubated at 20° C.

| Antifungal composition | Incubation time (days) | Observed antifungal activity O (%) | Expected antifungal activity E (%) | Synergy factor O/E |
|---|---|---|---|---|
| Control | 23 | 0 | — | — |
| Natamycin 50 ppm | | 12 | — | — |
| Cyprodinil 250 ppm | | 0 | — | — |
| Natamycin 50 ppm + cyprodinil 250 ppm | | 28 | 12 | 2.3 |
| Control | 29 | 0 | — | — |
| Natamycin 50 ppm | | 4 | — | — |
| Cyprodinil 250 ppm | | 0 | — | — |
| Natamycin 50 ppm + cyprodinil 250 ppm | | 25 | 4 | 6.3 |
| Control | 32 | 0 | — | — |
| Natamycin 50 ppm | | 1 | — | — |
| Cyprodinil 250 ppm | | 0 | — | — |
| Natamycin 50 ppm + cyprodinil 250 ppm | | 19 | 1 | 19 |
| Control | 36 | 0 | — | — |
| Natamycin 50 ppm | | 0 | — | — |
| Cyprodinil 250 ppm | | 0 | — | — |
| Natamycin 50 ppm + cyprodinil 250 ppm | | 10 | 0 | >10 |

TABLE 6

Antifungal activity (%) of compositions comprising either 250 ppm natamycin, 500 ppm pyrimethanil or both on bananas incubated at 20° C.

| Antifungal composition | Incubation time (days) | Observed antifungal activity O (%) | Expected antifungal activity E (%) | Synergy factor O/E |
|---|---|---|---|---|
| Control | 23 | 0 | — | — |
| Natamycin 250 ppm | | 19 | — | — |
| Pyrimethanil 500 ppm | | 0 | — | — |
| Natamycin 250 ppm + pyrimethanil 500 ppm | | 28 | 19 | 1.5 |
| Control | 29 | 0 | — | — |
| Natamycin 250 ppm | | 9 | — | — |
| Pyrimethanil 500 ppm | | 0 | — | — |
| Natamycin 250 ppm + pyrimethanil 500 ppm | | 13 | 9 | 1.5 |
| Control | 32 | 0 | — | — |
| Natamycin 250 ppm | | 2 | — | — |
| Pyrimethanil 500 ppm | | 0 | — | — |
| Natamycin 250 ppm + pyrimethanil 500 ppm | | 10 | 2 | 5.0 |

TABLE 6-continued

Antifungal activity (%) of compositions comprising either 250 ppm natamycin, 500 ppm pyrimethanil or both on bananas incubated at 20° C.

| Antifungal composition | Incubation time (days) | Observed antifungal activity O (%) | Expected antifungal activity E (%) | Synergy factor O/E |
|---|---|---|---|---|
| Control | 34 | 0 | — | — |
| Natamycin 250 ppm | | 0 | — | — |
| Pyrimethanil 500 ppm | | 0 | — | — |
| Natamycin 250 ppm + pyrimethanil 500 ppm | | 11 | 0 | >11 |

TABLE 7

Antifungal activity (%) of compositions comprising either 250 ppm natamycin, 500 ppm pyrimethanil or both on strawberries incubated at 20° C.

| Antifungal composition | Incubation time (days) | Observed antifungal activity O (%) | Expected antifungal activity E (%) | Synergy factor O/E |
|---|---|---|---|---|
| Control | 1 | 0 | — | — |
| Natamycin 250 ppm | | 25 | — | — |
| Pyrimethanil 500 ppm | | 0 | — | — |
| Natamycin 250 ppm + pyrimethanil 500 ppm | | 50 | 25 | 2.0 |
| Control | 2 | 0 | — | — |
| Natamycin 250 ppm | | 31 | — | — |
| Pyrimethanil 500 ppm | | 0 | — | — |
| Natamycin 250 ppm + pyrimethanil 500 ppm | | 52 | 31 | 1.7 |
| Control | 3 | 0 | — | — |
| Natamycin 250 ppm | | 24 | — | — |
| Pyrimethanil 500 ppm | | 0 | — | — |
| Natamycin 250 ppm + pyrimethanil 500 ppm | | 38 | 24 | 1.6 |

TABLE 8

Antifungal activity (%) of compositions comprising either 250 ppm natamycin, 500 ppm cyprodinil or both on mandarins incubated at 20° C.

| Antifungal composition | Incubation time (days) | Observed antifungal activity O (%) | Expected antifungal activity E (%) | Synergy factor O/E |
|---|---|---|---|---|
| Control | 16 | 0 | — | — |
| Natamycin 250 ppm | | 15 | — | — |
| Cyprodinil 500 ppm | | 60 | — | — |
| Natamycin 250 ppm + cyprodinil 500 ppm | | 97 | 66 | 1.5 |
| Control | 19 | 0 | — | — |
| Natamycin 250 ppm | | 5 | — | — |
| Cyprodinil 500 ppm | | 38 | — | — |
| Natamycin 250 ppm + cyprodinil 500 ppm | | 92 | 41 | 2.3 |
| Control | 22 | 0 | — | — |
| Natamycin 250 ppm | | 5 | — | — |
| Cyprodinil 500 ppm | | 20 | — | — |
| Natamycin 250 ppm + cyprodinil 500 ppm | | 86 | 24 | 3.5 |
| Control | 26 | 0 | — | — |
| Natamycin 250 ppm | | 5 | — | — |
| Cyprodinil 500 ppm | | 13 | — | — |
| Natamycin 250 ppm + cyprodinil 500 ppm | | 73 | 17 | 4.3 |

TABLE 9

Antifungal activity (%) of compositions comprising either 500 ppm natamycin, 1000 ppm pyrimethanil or both on mandarins incubated at 20° C.

| Antifungal composition | Incubation time (days) | Observed antifungal activity O (%) | Expected antifungal activity E (%) | Synergy factor O/E |
|---|---|---|---|---|
| Control | 22 | 0 | — | — |
| Natamycin 500 ppm | | 37 | — | — |
| Pyrimethanil 1000 ppm | | 82 | — | — |
| Natamycin 500 ppm + pyrimethanil 1000 ppm | | 100 | 89 | 1.1 |
| Control | 26 | 0 | — | — |
| Natamycin 500 ppm | | 30 | — | — |
| Pyrimethanil 1000 ppm | | 79 | — | — |
| Natamycin 500 ppm + pyrimethanil 1000 ppm | | 98 | 85 | 1.1 |

TABLE 10

Antifungal activity (%) of compositions comprising either 250 ppm natamycin, 500 ppm pyrimethanil or both on mandarins incubated at 20° C.

| Antifungal composition | Incubation time (days) | Observed antifungal activity O (%) | Expected antifungal activity E (%) | Synergy factor O/E |
|---|---|---|---|---|
| Control | 19 | 0 | — | — |
| Natamycin 250 ppm | | 5 | — | — |
| Pyrimethanil 500 ppm | | 84 | — | — |
| Natamycin 250 ppm + pyrimethanil 500 ppm | | 100 | 85 | 1.2 |
| Control | 22 | 0 | — | — |
| Natamycin 250 ppm | | 5 | — | — |
| Pyrimethanil 500 ppm | | 74 | — | — |
| Natamycin 250 ppm + pyrimethanil 500 ppm | | 96 | 75 | 1.3 |
| Control | 26 | 0 | — | — |
| Natamycin 250 ppm | | 5 | — | — |
| Pyrimethanil 500 ppm | | 65 | — | — |
| Natamycin 250 ppm + pyrimethanil 500 ppm | | 96 | 67 | 1.4 |

TABLE 11

In vitro antifungal activity (%) of natamycin in combination with cyprodinil or pyrimethanil against *Botrytis cinerea* after 5 days of incubation at 25° C.

| Antifungal composition | Observed antifungal activity O (%) | Expected antifungal activity E (%) | Synergy factor O/E |
|---|---|---|---|
| Control | 0 | — | — |
| Natamycin 0.63 ppm | 0 | — | — |
| Cyprodinil 20 ppm | 0 | — | — |
| Pyrimethanil 30 ppm | 50 | — | — |
| Natamycin 0.63 ppm + cyprodinil 20 ppm | 100 | 0 | >100 |
| Natamycin 0.63 ppm + pyrimethanil 30 ppm | 100 | 50 | 2 |
| Control | 0 | — | — |
| Natamycin 1.25 ppm | 0 | — | — |
| Cyprodinil 10 ppm | 0 | — | — |
| Pyrimethanil 17.5 ppm | 50 | — | — |
| Natamycin 1.25 ppm + cyprodinil 10 ppm | 100 | 0 | >100 |
| Natamycin 1.25 ppm + pyrimethanil 17.5 ppm | 100 | 50 | 2 |

TABLE 12

In vitro antifungal activity (%) of natamycin in combination with cyprodinil or pyrimethanil against *Fusarium proliferatum* after 5 days of incubation at 25° C.

| Antifungal composition | Observed antifungal activity O (%) | Expected antifungal activity E (%) | Synergy factor O/E |
|---|---|---|---|
| Control | 0 | — | — |
| Natamycin 1.25 ppm | 0 | — | — |
| Cyprodinil 125 ppm | 0 | — | — |
| Natamycin 1.25 ppm + cyprodinil 125 ppm | 100 | 0 | >100 |
| Control | 0 | — | — |
| Natamycin 2.5 ppm | 0 | — | — |
| Pyrimethanil 275 ppm | 0 | — | — |
| Natamycin 2.5 ppm + pyrimethanil 275 ppm | 100 | 0 | >100 |

REFERENCES

Colby S R (1967), Calculating synergistic and antagonistic responses of herbicide combination. Weeds 15: 20-22.

Kanetis L, Förster H, Jones C A, Borkovich K A and Adaskaveg J E (2008), Characterization of genetic and biochemical mechanisms of fludioxonil and pyrimethanil resistance in field isolates of *Penicillium digitatum*. Phytopathology 98: 2005-214.

Lapeyre de Bellaire de L and Dubois C (1987), Distribution of Thiabendazole-Resistant *Colletotrichum musae* Isolates from Guadeloupe Banana Plantations. Plant disease 81:1378-1383.

Moyano C, Gomez V and Melgarejo P (2004), Resistance to pyrimethanil and other fungicides in *Botrytis cinerea* populations collected on vegetable crops in Spain. J. Phytopathology 152: 484-490.

Slinker B K (1998), The Statistics of Synergism. Journal of Mol. and Cell. Cardiology 30:723-731.

Xiao C L, Kim Y K and Boal R J (2011), First report of occurrence of pyrimethanil resistance in *Penicillium expansu*, from stored apples in Washington State. Plant Disease 95: 72.

The invention claimed is:

1. A composition comprising natamycin and at least one antifungal compound selected from the group consisting of cyprodinil and pyrimethanil.

2. A composition according to claim 1, wherein the composition further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant.

3. A composition according to claim 1, wherein the amount of natamycin is in a range from 0.005 g/l to about 100 g/l and the amount of the at least one antifungal compound is in a range from about 0.0001 g/l to about 2000 g/l.

4. The composition of claim 1 which comprises natamycin and cyprodinil.

5. The composition of claim 4 wherein the amount of natamycin is in the range of 0.63 to 500 ppm, and the amount of cyprodinil is in the range of 10 ppm to 1000 ppm.

6. The composition of claim 1 which comprises natamycin and pyrimethanil.

7. The composition of claim 6 wherein the amount of natamycin is in the range of 0.63 to 500 ppm, and the amount of pyrimethanil is in the range of 17.5 ppm to 1000 ppm.

8. A kit comprising natamycin and at least one antifungal compound selected from the group consisting of cyprodinil and pyrimethanil.

9. A product comprising natamycin and at least one antifungal compound selected from the group consisting of cyprodinil and pyrimethanil.

10. A product according to claim 9, wherein said product is selected from the group consisting of a food product, a feed product, a pharmaceutical product, a cosmetic product and an agricultural product.

11. A product according to claim 10, wherein said product is an agricultural product.

12. A method for protecting a product against fungi comprising treating the product with natamycin and at least one antifungal compound selected from the group consisting of cyprodinil and pyrimethanil.

13. A method according to claim 12, wherein said product is selected from the group consisting of a food product, a feed product, a pharmaceutical product, a cosmetic product and an agricultural product.

14. A method according to claim 13, wherein said product is an agricultural product.

15. A method according to claim 14, wherein said product is treated post-harvest.

16. A method according to claim 12, wherein said product is treated with a composition comprising natamycin and at least one antifungal compound selected from the group consisting of cyprodinil and pyrimethanil.

17. A method according to claim 16, wherein said product is selected from the group consisting of a food product, a feed product, a pharmaceutical product, a cosmetic product and an agricultural product.

* * * * *